(12) United States Patent
Chu

(10) Patent No.: US 7,725,193 B1
(45) Date of Patent: May 25, 2010

(54) INTRAMUSCULAR STIMULATION THERAPY USING SURFACE-APPLIED LOCALIZED ELECTRICAL STIMULATION

(75) Inventor: Jennifer Chu, Haverford, PA (US)

(73) Assignee: Jus-Jas LLC, Haverford, PA (US)

( * ) Notice: Subject to any disclaimer, the term of this patent is extended or adjusted under 35 U.S.C. 154(b) by 930 days.

(21) Appl. No.: 11/470,757

(22) Filed: Sep. 7, 2006

Related U.S. Application Data

(60) Provisional application No. 60/715,137, filed on Sep. 9, 2005, provisional application No. 60/834,184, filed on Jul. 31, 2006.

(51) Int. Cl.
*A61N 1/00* (2006.01)
(52) U.S. Cl. .................................................. 607/48
(58) Field of Classification Search ............... 607/48
See application file for complete search history.

(56) References Cited

U.S. PATENT DOCUMENTS

| | | | |
|---|---|---|---|
| 4,180,079 | A | 12/1979 | Wing |
| 4,276,879 | A | 7/1981 | Yiournas |
| 4,613,328 | A | 9/1986 | Boyd |
| 4,662,363 | A | 5/1987 | Romano et al. |
| 4,758,227 | A | 7/1988 | Lancaster, Jr. et al. |
| 5,199,952 | A | 4/1993 | Marshall, Sr. et al. |
| 5,211,175 | A | 5/1993 | Gleason et al. |
| 5,466,247 | A * | 11/1995 | Scheiner et al. ............... 607/48 |
| 5,535,746 | A | 7/1996 | Hoover et al. |
| 5,735,868 | A | 4/1998 | Lee |
| 5,968,063 | A | 10/1999 | Chu et al. |
| 6,026,328 | A * | 2/2000 | Peckham et al. ............... 607/48 |
| 6,058,938 | A | 5/2000 | Chu et al. |
| 6,175,764 | B1 | 1/2001 | Loeb et al. |
| 6,181,965 | B1 | 1/2001 | Loeb et al. |
| 6,532,390 | B1 | 3/2003 | Chu et al. |

OTHER PUBLICATIONS

C. Chan Gunn, M.D., "The Gunn Approach to the Treatment of Chronic Pain: Intramuscular Stimulation for Myofascial Pain of Radiculopathic Origin", (2d ed.), 1996.

(Continued)

*Primary Examiner*—George Manuel
(74) *Attorney, Agent, or Firm*—Banner & Witcoff, Ltd

(57) ABSTRACT

A modality of electrical twitch obtaining intramuscular stimulation pain relief therapy utilizes a surface probe with a conductive tip to apply surface electrical stimulation of relatively high voltage locally and focally to muscle motor points and regions of adjacent motor end plate zones. The surface-applied electrical stimulation through intact skin readily facilitates the elicitation of forceful twitch responses from muscle fibers associated with the stimulated motor points and motor end plate zones, without requiring needle penetration into the patient's flesh. Rapid movement between multiple treatment sites is possible allowing treatment of a larger number of muscle motor point areas in afflicted muscles and more muscles to be treated in a single treatment session. The therapeutic effect of the twitches increases with the force and number of the twitches. In addition, since physical insertion of the needle electrode is totally unnecessary, patients experience little to no pain during and after the procedure, and the risk of repetitive stress injury to the therapist is reduced. Additionally, significantly less skill is required to effectively elicit pain relieving twitch responses, thus facilitating training of medical and para-medical personnel to perform the procedure.

20 Claims, 1 Drawing Sheet

OTHER PUBLICATIONS

Ghoname EA. Craig WF. White PF. Ahmed HE. Hamza MA. Henderson BN. Gajraj NM. Huber PJ. Gatchel RJ. Percutaneous Electrical Nerve Stimulation for Low Back Pain: A Randomized Crossover Study. JAMA. 281(9):818-23, Mar. 3, 1999.

Yokoyama M. Sun X. Oku S. Taga N. Sato K. Mizobuchi S. Takahashi T. Morita K. Comparison of Percutaneous Electrical Nerve Stimulation with Transcutaneous Electrical Nerve Stimulation for Long-term Pain Relief in Patients with Chronic Low Back Pain. *Anesthesia & Analgesia.* 98(6):1552-6, Jun. 2004.

Minder PM. Noble JG. Alves-Guerreiro J. Hill ID. Lowe AS. Walsh DM. Baxter GD. Interferential therapy: lack of effect upon experimentally induced delayed onset muscle soreness. *Clinical Physiology & Functional Imaging.* 22(5):339-47, Sep. 2002.

Werners R., Pynsent PB., Bulstrode CJ: Randomized Trial Comparing Interferential Therapy with Motorized Lumbar Traction and Massage in the Management of Low Back Pain in a Primary Care Setting. *Spine.* 24(15):1579-84, Aug. 1, 1999.

Popovic M.R. Keller T. Modular transcutaneous functional electrical stimulation system. [Case Reports. Journal Article] *Medical Engineering & Physics.* 27(1):81-92, Jan. 2005).

Koke A.J. Schouten JS. Lamerichs-Geelen MJ. Lipsch JS. Waltje EM. van Kleef M. Patijn J. Pain reducing effect of three types of transcutaneous electrical nerve stimulation in patients with chronic pain: a randomized crossover trial. *Pain.* 108(1-2):36-42, Mar. 2004.

Chu J: Twitch Response in Myofascial Trigger Points. J Musculoske Pain 6(4), 99-110, 1998.

Chu J: Twitch-obtaining intramuscular stimulation (TOIMS) in acute partial radial nerve palsy. Electromyogr Clin Neurophysiol 39:221-226, 1999.

Chu J: The role of the monopolar electromyographic pin in myofascial pain therapy: automated twitch-obtaining intramuscular stimulation (ATOIMS$^{SM}$) and electrical twitch-obtaining intramuscular stimulation (ETOIMS$^{SM}$)- Electromyogr Clin Neurophysiol 39: 503-511, 1999.

Chu J: Twitch-Obtaining Intramuscular Stimulation: Observations in the Management of Radiculopathic Chronic Low Back Pain. J Musculoske Pain 7(4): 131-146, 1999.

Chu J: Twitch obtaining intramuscular stimulation (TOIMS): Long-term observations in the management of chronic partial cervical radiculopathy. Electromyogr Clin Neurophysiol 40:503-510, 2000.

Gozon B, Chu J, Schwartz I: Lumbosacral radiculopathic pain presenting as groin and scrotal pain: Pain management with twitch-obtaining intramuscular stimulation. A case report and review of literature. Electromyogr Clin Neurophysiol 41:315-318, 2001.

Chu J, Gozon B, Schwartz I: Twitch-Obtaining Intramuscular Stimulation in Reflex Sympathetic Dystrophy. Electromyogr Clin Neurophysiol 42:259-22, 2002.

Chu J: The muscle twitch in myofascial pain relief: effects of acupuncture and other needling methods. Electromyogr Clin Neurophysiol 42:307-311, 2002.

Chu J: The local mechanism of Acupuncture. Chinese Medical Journal (Taipei) 65:299-302 2002.

Chu J, Neuhauser D, Schwartz I, Aye HH: The efficacy of automated/electrical twitch obtaining intramuscular stimulation (ATOIMS/ETOIMS) for chronic pain control : Evaluation with statistical process control methods. Electromyogr clin Neurophysiol 42:393-401, 2002.

Chu J, Yuen KF, Wang BH, Chan RC, Schwartz I, Neuhauser D: Electrical Twitch-Obtaining Intramuscular Stimulation in Lower Back Pain: A Pilot Study. Am J Phys Med Rehabil 83, No. 2: 104-111, 2004.

Chu J et al: Efficacy of Electrical Twitch Obtaining Intramuscular Stimulation (ETOIMS) in Chronic Neck Pain (CNP). (abstract accepted for presentation at American Academy of Physical Medicine and Rehabilitation, Oct. 2005.

Chu J et al: Efficacy of Electrical Twitch Obtaining Intramuscular Stimulation (ETOIMS) in Chronic Lower Back Pain (CLBP). (abstract accepted for presentation at American Academy of Physical Medicine and Rehabilitation, Oct. 2005.

Chu, J., "Dry Needling (Intramuscular Stimulation) in Myofascial Pain Related to Lumbosacral Radiculopathy", Eur. J. Phys. Med. Rehabil. 1995: 5 No. 4, pp. 106-120.

Chu, J., Comment on the Simmons Literature Review Column, 'Myofascial Pain Syndrome—Trigger Points', J. Musculoskeletal Pain, vol. 5(1) 1997, pp. 133-135.

Photographs of IMS device purchased from Mr. Young H. Lee in Feb. 1996.

C.C. Gunn, et al., "Dry Needling of Muscle Motor Points for Chronic Low-Back Pain: A Randomized Clinical Trial With Long Term Follow-Up", Spine, vol. 5, No. 3, May/Jun. 1980, pp. 279-291.

C Chan Gunn, "Treating Myofascial Pain: Intramuscular Stimulation (IMS) for Myofascial Pain Syndromes of Neuropath Origin", 1989.

Open Letter re IMS treatment offered by Jennifer Chu,M.D., University of Pennsylvania Medical Center, Mar. 13, 1996.

"Patient Information on Intramusclular Stimulation (IMS) for Management of Soft-Tissue/Neuropathic Pain", University of Pennsylvania Medical Center, Apr. 8, 1996.

Travell, J.G., Simons, D.G., "Myofascial Pain and Dysfunction: The Trigger Point Manual", vol. 1. Williams and Wilkins, Baltimore, 1983, Table of Contents, Preface, Chapter 3 "Apropos of all Muscles".

Travell, J.G., Simons, D.G., "Myofascial Pain and Dysfunction: The Trigger Point Manual", vol. 2. The Lower Extremities. Williams and Wilkins, Baltimore, 1992, Table of Contents, Chapter 2 "General Issues".

Stålberg, E., Trontelj, J., "Single Fiber Electromyography, Studies in Healthy and Diseased Muscle", 2d Ed., Raven Press Ltd., New York (1994).

Chu, J. "Does EMG (dry needling) reduce myofacial pain symptoms due to cervical nerve root irritation?" Electromyogr. clin. Neurophysiol., 37:259-272, 1997.

Chu, J. "Twitch-Obtaining Intramuscular Stimulation: Its Effectiveness in the Long-Term Treatment of Myofascial Pain Related to Lumbosacral Radiculopathy", Arch. Phys. Med. Rehabil., 78:1024, Sep. 1997 (abstract).

Chu, J. "Twitch-Obtaining Intramuscular Stimulation: Effective for Long-Term Treatment Myofascial Pain Related to Cervical Radiculopathy", Arch. Phys. Med. Rehabil., 78:1042, Sep. 1997 (abstract).

The NeuroControl StIm™ System Clinician Manual, Neuro Control Corp., 1999-2000.

* cited by examiner

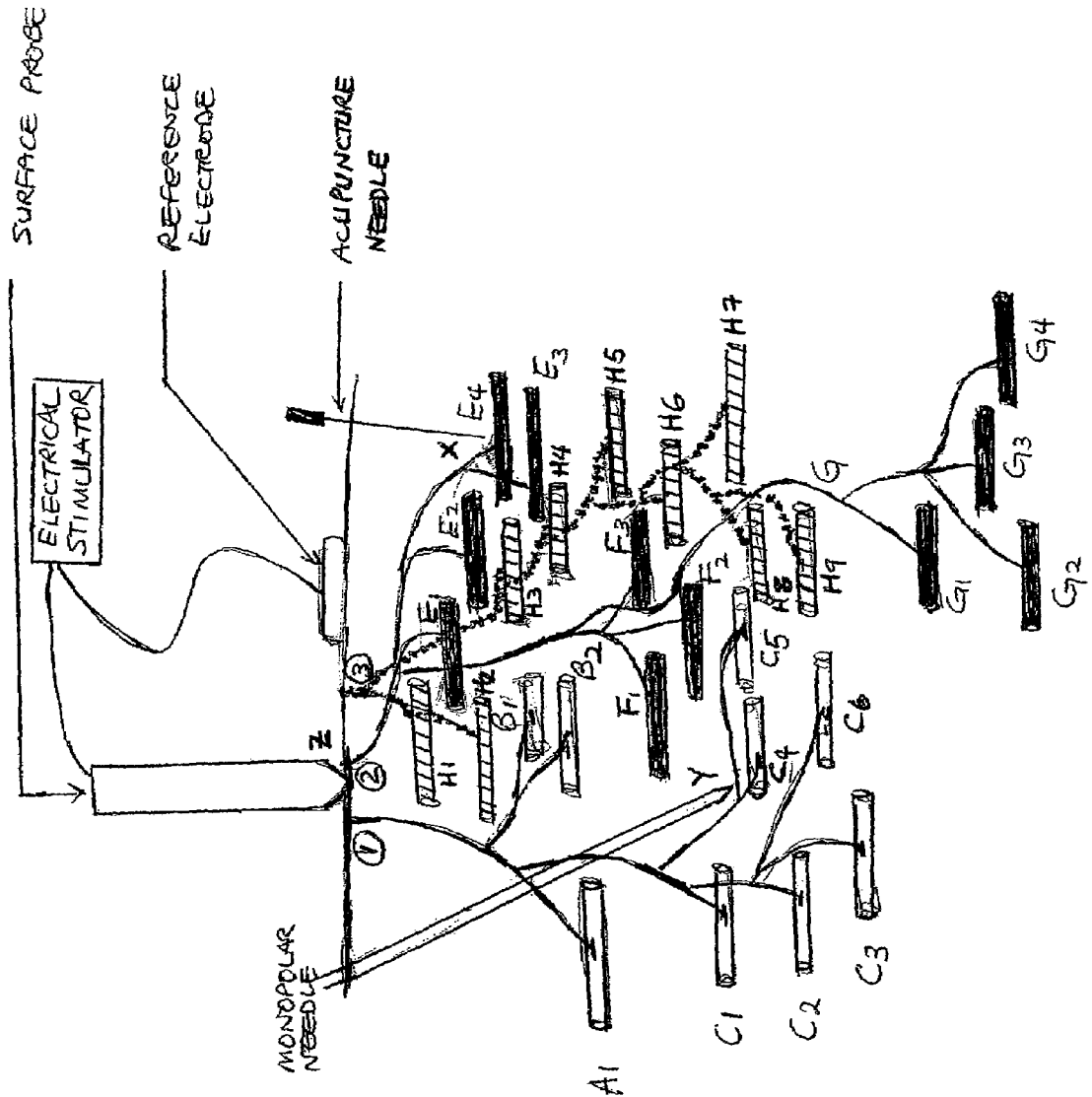

INTRAMUSCULAR STIMULATION THERAPY USING SURFACE-APPLIED LOCALIZED ELECTRICAL STIMULATION

This application claims the benefit of co-pending U.S. provisional application Ser. No. 60/715,137, filed Sep. 9, 2005. The substance of this provisional application is substantially bodily incorporated herein. Any substantive aspect of the provisional application not bodily incorporated herein is hereby incorporated by reference, to thereby assure complete carry-forward of the supporting disclosure of the provisional application. This application also claims the benefit of copending provisional application Ser. No. 60/834,184, filed Jul. 31, 2006, entitled "Bipolar Stimulation/Recording Device With Widely Spaced Electrodes." This provisional application is, in its entirety, hereby incorporated by reference.

FIELD OF THE INVENTION

The present invention relates to nerve root related muscle pain and muscle discomfort management. In particular, the invention relates to intramuscular stimulation therapy utilizing localized electrical stimulation to help relieve acute, sub-acute and chronic nerve-related muscle pain, including but not limited to pain for which a specific cause cannot be determined, and for which medicinal and other usual methods of pain relief have proven ineffective. It will be understood that, except as otherwise indicated, "pain" as used herein broadly encompasses chronic nerve related muscle pain as well as manifestations of muscle discomfort such as soreness, stiffness, swelling, aching, tightness, tenderness and tautness of muscles.

BACKGROUND OF THE INVENTION

Conventional pain management is directed toward treating the symptom and not the cause of pain. Conventional methods of treating pain include, as broad categories: (1) oral non-narcotic and/or narcotic medications, (2) physical therapy, (3) chiropractic manipulation, (4) epidural injections or nerve-root blocks, (5) radio-frequency denervation, (6) disc coblation, (7) Intradiscal Electrothermal Annuloplasty and last but not least (8) micro or conventional open spinal surgery. Most of these techniques can be used only for a limited number of times and are not helpful in the long-term management of chronic myofascial pain. The management of chronic pain due to repetitive strain injuries is a $120 billion dollar business in the United States, by 1994 estimates of the U.S. Occupational Safety and Health Administration (OSHA). Low back pain alone is a leading cause for physician visits, second only to the common cold. Neurophysiologically and anatomically based pain management methods that do not use drugs are an effective alternative to conventional care.

It is well established that electrical stimulation may be used to augment needle based pain relief treatments, including acupuncture, IMS therapy, percutaneous electrical nerve stimulation (PENS), transcutaneous electrical nerve stimulation (TENS), and use of interferential current. Surface electrical stimulation termed functional electrical stimulation (FES) is also available for stimulating muscles paralysed due to a stroke or spinal cord injury. Electrical muscle stimulators (EMS devices) and neuromuscular electrical stimulators (NMES) are also readily available commercially.

In electro-acupuncture, stainless steel acupuncture pins serving as electrode pairs are supplied with constant or pulsed direct current. The pins are placed into traditional acupuncture points along traditional imaginary meridians. Electrical stimulus parameters are similar as in percutaneous electrical nerve stimulation (PENS) as described below.

The basic PENS therapy consisted of the placement of ten 32-gauge stainless steel acupuncture-like needle probes into the soft tissue and/or muscle to a 2- to 4-cm depth according to the dermatomal distribution of the pain. The needle probes connect to five bipolar leads (with each lead connected to one positive and one negative probe) from a low-output (<25 mA) electrical generator, which produced a unipolar square-wave pattern of electrical stimulation at a frequency of 4 Hz with a pulse width of 0.5 milliseconds. The intensity of the electrical stimulation is adjusted to produce the maximum tolerable "tapping" sensation without muscle contractions. (reference #2. Ghoname E A. Craig W F. White P F. Ahmed H E. Hamza M A. Henderson B N. Gajraj N M. Huber P J. Gatchel R J. Percutaneous electrical nerve stimulation for low back pain: a randomized crossover study. *JAMA*. 281(9):818-23, 1999 Mar. 3).

Basic PENS therapy may also consist of the placement of ten 32-gauge (0.2-mm) stainless steel acupuncture-like needle probes (ITO, Tokyo, Japan) into the soft tissue or muscle in the low back region to a depth of 2-4 cm according to the dermatomal distribution of the pain. The needle probes connect to five bipolar leads (with each lead connected to one positive and one negative probe) from a low-output electrical generator, calibrated before each series of treatments. The electrical current is DC, and the duty cycle is continuous. These probes are stimulated at 4/30 Hz for 20 min. The intensity of the electrical stimulation is adjusted to produce the most intense tolerable electrical sensation without muscle contractions. (Yokoyama M. Sun X. Oku S. Taga N. Sato K. Mizobuchi S. Takahashi T. Morita K. Comparison of percutaneous electrical nerve stimulation with transcutaneous electrical nerve stimulation for long-term pain relief in patients with chronic low back pain. *Anesthesia & Analgesia*. 98(6): 1552-6, 2004 June.

Surface applied electrical stimulation known as Interferential therapy (IT) is claimed to work by stimulating muscle fibers. This is presumed to improve the circulation, thus bringing about faster healing of the muscles. IT is stated to speed the healing process by delivering small pulses of electrical current to an injury through electrodes that pass current through the skin and stimulate underlying nerves producing a mild, tingling sensation to provide relief from chronic and acute pain. IF is used for very localized areas where deep current for pain control or increased circulation is needed. Traditional IT uses the principle of mixing a 4 kHz and a 4.001-4.005 kHz frequency to generate the single desired frequency of 1-1000 Hz. The therapeutic frequency moves up and down between 30-60 Hz. to 80-100 Hz [bi-pole; carrier frequency: 4 kHz; pulse duration: 125 microseconds]. (Minder P M. Noble J G. Alves-Guerreiro J. Hill I D. Lowe A S. Walsh D M. Baxter G D. Interferential therapy: lack of effect upon experimentally induced delayed onset muscle soreness. *Clinical Physiology & Functional Imaging*. 22(5): 339-47, 2002 September; Werners R., Pynsent P B., Bulstrode C J: Randomized trial comparing interferential therapy with motorized lumbar traction and massage in the management of low back pain in a primary care setting. *Spine*. 24(15): 1579-84, 1999 Aug. 1.

IT employs a stimulator used for muscle contraction. However as in TENS, with IT stimulation, the muscle will also contract weakly and non-specifically, rather as a muscle pumping motion, in response to the electrical stimulus given at high frequency. These are not the true active muscle contraction via a specific motor end-plate zone activation that cause the muscle to suddenly "jump," as is sought and obtainable with ATOIMS and ETOIMS (as well as the present inventive SA-ETOIMS technique). This pumping type of contraction continues until the IT unit is turned off after 20 minutes or longer according to the patient's tolerance.

Functional electrical stimulation (FES), also a surface applied method of electrical stimulation therapy, is delivered via the Compex Motion electric stimulator for stimulation of paralysed muscles due to a stroke or spinal cord injuries. The Compex Motion stimulator was designed to serve as a hardware platform for development of diverse FES systems that apply transcutaneous (surface) stimulation technology. It is a microcontroller-based system with four stimulation channels, two input channels A and B, and a special purpose port C. The stimulation channels are current regulated and have 3 µs rise time for pulses with 125 mA amplitudes (pulse amplitude range 0-125 mA, resolution 1 mA; pulse width range 0-16 ms, resolution 500 η-long pulse widths such as 16 ms may be used to stimulate denervated muscles; and stimulation frequency 1-100 Hz, resolution 1 Hz). The input channels A and B can be configured as analog or digital input channels (maximum sampling frequency 8 kHz, voltage range 0-5 V and resolution 20 mV). The special purpose port C is used to interconnect the stimulators, to serially communicate with a PC, and to trigger the stimulator using a push button. By interconnecting stimulators via port C, one can expand the number of stimulation channels from four to multiples of four channels. In such a configuration, one stimulator is designated as a master stimulator while all other stimulators are designated as slaves. The master stimulator paces the stimulation of all connected stimulators and ensures that all stimulators are synchronized and maintain the same "bus frequency" during the entire stimulation protocol. The Compex Motion has a dot matrix LED display that provides a visual interface between the user and the stimulator. (Popovic MR. Keller T. Modular transcutaneous functional electrical stimulation system. *Medical Engineering & Physics.* 27(1):81-92, 2005 January.)

FES surface electrical stimulation is primarily used for denervated or paralysed muscles because of loss of nerve control as from a stroke or spinal cord injury. The entire muscle contracts when stimulation occurs simultaneously at multiple motor points causing movement of a joint for functional purposes. Muscle groups can be stimulated in overlapping fashion to produce a pumping action. The stimulus frequency is high and is in the range of 1-100 Hz, with very long pulse widths of 16 ms and the stimulation may continue as much as for 6 hours, six days a week. An example would be that of stimulation of the quadriceps, a group of four muscles in the front of the thigh into contraction and to stimulate it long enough hold the contraction in order to keep the knee in extension for use in walking.

Transcutaneous electrical nerve stimulation (TENS) applied onto the skin surface for stimulation of skin nerve fibers is used also in chronic pain management. The stimulus parameters in the high frequency conventional TENS uses frequency 80 Hz, pulse duration 80 µs and patients are instructed to use TENS 4-6 times a day for 1-h periods at sensory threshold intensity. In the high frequency high-intensity TENS group (HIT; frequency 80 Hz, pulse duration 250 µs), patients are instructed to use TENS 4-6 times a day for 30-min periods at maximum tolerated intensity level. In the control TENS group (COT; frequency 30 Hz, pulse duration 250 µs) patients were free to choose stimulus duration and stimulus intensity as they preferred. Two TENS-devices were used: TWIN-STAR (van Lent Systems B.V. Netherlands), TENStem (Schwa Medico Netherlands). Koke A J. Schouten J S. Lamerichs-Geelen M J. Lipsch JS. Waltje E M. van Kleef M. Patijn J. Pain reducing effect of three types of transcutaneous electrical nerve stimulation in patients with chronic pain: a randomized crossover trial. *Pain.* 108(1-2):36-42, 2004 March.

Standard TENS therapy consisted of the placement of 4 medium-sized (2.5-cm) cutaneous electrode pads in a standardized dermatomal pattern. These electrodes were also stimulated at a frequency of 4/30 Hz for 20 min. (Yokoyama M. Sun X. Oku S. Taga N. Sato K. Mizobuchi S. Takahashi T. Morita K. Comparison of percutaneous electrical nerve stimulation with transcutaneous electrical nerve stimulation for long-term pain relief in patients with chronic low back pain. *Anesthesia & Analgesia.* 98(6):1552-6, 2004 June).

Usually the stimulation is for excitation of skin receptors only, but frequently the underlying muscle will also contract weakly and non-specifically, rather as a muscle pumping motion, in response to the electrical stimulus over a superficial motor point. These are not the true muscle contractions that cause a sudden muscle "jump" needed to produce a therapeutic effect with twitches as in the present inventor's ATOIMS and ETOIMS techniques (as well as the new SA-ETOIMS technique described herein). The pumping type of contraction produced with the TENS unit continues until the TENS unit is turned off. Usually a TENS treatment lasts 20 minutes or up to a few hours according to the patient's tolerance.

Many electrical muscle stimulators (EMS), such as neuromuscular stimulators (NMS) or high voltage galvanic stimulator (HVGS) using direct or alternating currents, are commercially available. These devices are used to maintain or increase range of motion, re-educate muscles, relax spasms, and increase local blood circulation. Surface applied electrical muscle stimulators units can deliver up to 100 mamp or up to 350 volts to a very low skin impedance load (500-1000 ohms) and are thus capable of producing only non-specific superficial muscle pumping motion continuously or in trains. Additionally, the stimulus frequency in electrical muscle stimulators range from 1-5000 Hz and are designed to contract the muscle through causing a muscle spasm by using very high frequency stimulation briefly and then to allow the muscle to relax. egs. of commercially available electrical muscle stimulators are OMNISTIM® FX2, etc. If twitches are elicited at low frequencies, they are weak and non-specific electrically driven "pump" style contractions in contrast to the sudden "jump" style twitches that are elicited in ATOIMS and ETOIMS (as well as the new SA-ETOIMS technique described herein).

Nerve conduction studies (NCS) are performed by stimulating peripheral nerves through intact skin. These are diagnostic tests and are not used for pain relief. NCS uses stimulus intensities up to 300 volts (this is provided through an electromyographic (EMG) machine that provides constant voltage, maximum 300 volts). The NCS tests can also be performed with constant current stimulation strength up to 100 milliamps through using a different EMG machine that can provide constant current stimulation, with maximum output of 100 milliamp. The stimulus pulse width is 0.05-1 ms at a frequency of 1 Hz. NCS is a diagnostic test and major peripheral nerves are stimulated on the surface of the skin to determine their conductivity to the electrical stimulus. All muscles supplied by the stimulated peripheral nerve will contract and the joint moves forcibly due to contraction of muscles that cross the joint. The stimulus in nerve conduction studies is not isolated to stimulation of individual motor points on a single muscle and adjacent motor end-plate zones, as generally the case with the present inventor's ATOIMS and ETOIMS techniques (as well as the new SA-ETOIMS technique described herein).

Needle techniques used in conjunction with electrical stimulation for pain relief purposes are described below:

PENS and electrical acupuncture use low dose electrical current, and twitches if evoked are generally of relatively very small size since only a tapping motion of the needles is required and may evoke micro-twitches. The duration of the treatment session for electrical stimulation is not standardized and may vary from a few minutes to approximately twenty minutes, depending on the acupuncturist's style and subjective/empirical evaluations. In both PENS and acupuncture, the stimulus is delivered through wiry, stainless steel acupuncture needle insertion and the stimulus strength used is very small. (<25 mA, a unipolar square-wave pattern of electrical stimulation at a frequency of 4 Hz with a pulse width of 0.5 milliseconds). The electrical current is DC, and the duty cycle is continuous. These probes are stimulated at 4/30 Hz for 20 min. The intensity of the electrical stimulation is adjusted to produce the most intense tolerable electrical sensation generally without muscle contractions.

Gunn teaches in his 1996 text, supra, that electrical stimulation can be used in his IMS technique (focused on stimulation of clinical muscle motor points), in place of manual needle agitation, to hasten the release of muscle contracture (pp. 12 and 35-36). Specifically, Gunn teaches (at page 35) that a low-voltage (9-18 V) interrupted direct current may be administered for seconds or minutes to the inserted needle until muscle release is obtained. Gunn further teaches alternatively that the electrical stimulation may be applied for approximately 15-30 minutes, with the current being gradually increased until muscle contractions are visible to confirm that the needles are properly placed. The standard acupuncture pins used in electro-acupuncture and Gunn's IMS technique are conductive along their entire lengths. As a result, the electrical field that is established extends along the length of the inserted portion of the pin, and is dispersed into the skin and subcutaneous tissues, in addition to the target muscle area. The intensity of the electric field actually established at the target area is difficult to accurately calculate and control. Gunn's technique is to apply electrical stimulation for release of the tight muscle fibers in spasm. There is no mention of inducing active muscle contractions to elicit strong muscle twitches through focal muscle contractions as in ETOIMS. Given Gunn's focus on release of spasm within a given muscle, electrical stimulation is stopped once a release of spasm is obtained.

As described in the present inventor's U.S. Pat. No. 6,058,938, non-chemical, needle-applied electrical twitch obtaining intramuscular stimulation (ETOIMS) is used effectively in the management of regional and diffuse myofascial pain (fibromyalgia) of radiculopathic origin where musculoskeletal pain resulting from muscle shortening is the predominant feature. Unlike acupuncture, where many pins that remain stationary are inserted into points on imaginary meridians during a treatment session, in needle-applied ETOIMS generally only one needle (a monopolar electrode) is used at multiple muscle sites during one treatment session. The needle that is inserted into a tender muscle motor point, is used to electrically stimulate the motor end-plate zones to cause the muscle to twitch. The therapeutic effects are best obtained when twitches are forceful enough to either shake or move the joint upon which the muscle acts.

Needle-applied ETOIMS is focused on searching point by stimulated point in a muscle to elicit a strong twitch from active contraction of stimulated muscle fibers through most terminal nerve excitation. Needle-applied ETOIMS uses low frequency stimulus at 1-2 Hz with stimulus applied through a single Teflon coated monopolar needle electrode for 0.5 seconds per stimulated point. This technique is focused on evoking strong twitches. The therapeutic effect of the twitches increases with the force and number of the twitches elicited. Stimulus parameters for electrical intramuscular stimulation are 0.5-1.5 volts, pulse width 0.5 ms and frequency of 2 Hz. Each treatment point is stimulated for 0.5 seconds with fixed amplitude of the alternating current at 2 mA. Needle-applied ETOIMS stimulates the muscle at multiple points in the search for the motor end plate zone that will elicit the strongest force twitch responses at multiple (four or more) points within an afflicted muscle through a localized application of electrical stimulation to multiple motor end plate zones. The technique is applied to have a local focal exercise effect that restores muscle fiber length through a stretch effect. This helps to improve circulation to nerve and muscle in the areas stimulated.

In contrast to conventional pain management, needle-applied electrical twitch obtaining intramuscular stimulation (ETOIMS™), is an effective procedure that can be used repetitively throughout the lifetime of the chronic pain patient, without endangering the health of the patient or causing substantial adverse side effects. Needle-applied ETOIMS™ treats the cause of the muscle pain or muscle discomfort, i.e., muscles shortened or in spasm due to nerve root irritation. When the muscles are shortened due to spasm from nerve root irritation, the muscles pull or tug on adjacent structures to which they attach such as tendons, ligaments, bones, joints, and intervertebral discs. They also compress the intramuscular blood vessels and nerves. This relentless pulling or vice-like effect of the shortened muscles causes more nerve root irritation and more muscle shortening leading to a vicious cycle of acute, sub-acute or chronic nerve related muscle pain. By causing the muscles to twitch with electrical stimulation of the motor point and motor end plate zones, the shortened muscles are stretched and exercised from within the muscle leading to muscle relaxation following the twitch contraction. Muscle relaxation in turn leads to less tugging effect on the pain sensitive tendons, ligaments, bones, joints, intervertebral discs, onto which these muscles attach, and therefore pain reduction or relief of the discomfort is achieved. Successive treatments have a positive accumulative effect from active twitch-induced muscle exercise leading to progressive muscle relaxation. These twitch-induced muscle contractions and immediate relaxation effects allow the intramuscular nerves to heal when blood flow can resume into the relaxed muscle regions as opposed to those intramuscular nerves within taut and tight muscle regions.

Despite the effectiveness in ultimately providing pain relief, needle-applied ETOIMS treatments can be quite painful to the patient who is already in pain. The very nature of the procedure with its need for insertion of a needle, and then electrically stimulating the nerve to cause the muscle to twitch (contract and immediately relax with stretching effects) tends to deflect the needle causing more pain to the patient. The pain is also from the electricity that acts as an irritant to muscles when they are too tight to twitch. Multiple needle insertions are also required repeatedly into many muscles in the search for the motor endplate zones that will yield large force twitches. Oral ingestion of muscle relaxants or anti-anxiety agents, such as Valium (5-10 mgm), and a pain medication, such as 1-2 tablets of Percocet (Oxycodone 5 mg, and Tylenol, 375 mg/tablet) or Morphine Sulfate Immediate Release (MSIR), 15-30 mg, 1 hour before treatment or one unit of Actiq (transmucosal Fentanyl) 200-800 μgms at 15 minutes before treatment can be used to reduce procedural pain.

Even though needle-applied ETOIMS is performed using an automated device that inserts and immediately retracts the needle, the procedure is still laborious, tedious and time-consuming. This may lead to repetitive stress injury to the operator from the need to perform the treatment in a bi-manual fashion. One hand of the operator is used to hold and stabilize the muscle in position while the other hand is used to hold the device for accurate needle penetration into the motor end-plate zone region. The problem for the operator is particularly acute when, as is typically the case, many areas of a patient's body are to be treated in one session, and when the majority of the patients require this type of multi-area intensive treatment. Under these circumstances, the operator performing bi-manual ETOIMS on a long-term basis likely will suffer from repetitive strain injuries.

The present physician inventor has found needle-applied ETOIMS to be very effective in the acute and long-term management of nerve related muscle pain. However, due to use of an automated needling device for therapy, the training in anatomy, peripheral neurology and clinical aspects that has to be given to operators for safe application of treatments is intensive, rigorous, thorough and prolonged. This predictably limits the number of operators who can be trained in needle-applied ETOIMS method.

SUMMARY OF THE INVENTION

In view of the foregoing, it is a principal object of the present invention to improve the effectiveness of needle-applied electrical twitch obtaining IMS (ETOIMS™) pain relief therapy techniques, i.e., to increase and prolong the resultant pain relief, and reduce tissue trauma and patient discomfort associated with the needle-applied ETOIMS™ procedure. It is a more specific object of the invention to facilitate and expedite the performance of ETOIMS™ procedures, through a novel non-invasive approach which allows a larger number of afflicted muscle areas and many more afflicted muscles to be treated effectively in a treatment session, with less effort and risk of repetitive stress injury on the part of the treating physician or other therapist.

With needle-applied ETOIMS, a situation can arise where many motor end plates are refractory to electrical stimulation or that the needle may not have been inserted into the region of motor endplate zones. In this case, the patient has to undergo many painful needle-applied electrical stimulation unnecessarily to many points in the muscle. These multiple needle penetrations are needed in the search for the region with electrically sensitive motor end plate zones that can produce a twitch that shakes or moves the joint without changing the stimulus parameters at all stimulated points within the same muscle once a stimulus strength has been appropriately titrated. These difficulties are avoided with the non-invasive nature of the present inventive SA-ETOIMS technique, that can accomplish the goal of finding the region with excitable motor end plate zones through surface stimulation with specific stimulus parameters.

In SA-ETOIMS, as with needle applied ETOIMS, the stimulus intensity for motor points may be unchanged for all points within the same muscle while searching for the electrically sensitive motor point or motor end plate zones that will produce twitch forces strong enough to shake or move the joint over which the treated afflicted muscle acts. Since needle penetration is not required, SA-ETOIMS process is painless and the treatment sessions can be shorter since twitch elicitation is easier and quicker. Also, the ease or difficulty in finding the motor point can be used as a diagnostic aid for differentiating acute or chronic nerve related muscle disorders. In patients with chronic muscle tightness due to chronic spinal or peripheral nerve involvement, motor point localization is difficult. This is commonly noted in stimulating large muscles to identify the location of the motor points. In such situations, stimulus pulse width and stimulus strength have to be sufficiently high at all muscle points stimulated to ensure that the stimulus strength can reach and will be sufficient to excite the motor point to elicit twitch forces strong enough to shake or move the joint upon which the stimulated muscle acts. On the contrary, in patients with acute nerve related muscle disorders, the motor points are easily identified since use of a short duration pulse width at very low stimulus intensity will excite the motor points to elicit twitch forces that are strong enough to shake or move the joint upon which the stimulated muscle acts.

It is a related object of the invention to provide a simplified and standardized surface-applied electrical twitch obtaining intramuscular stimulation (SA-ETOIMS) procedure that medical personnel, including but not limited to physicians, can rapidly be trained in, thus making the procedure available at low cost and on a mass scale. This will lead to patients having reduced absenteeism at work, payout for workman's compensation, and disability expenses. And, a larger number of pain-afflicted persons may enjoy happier, more productive and fulfilling lives.

With the present new invention of surface-applied ETOIMS, which for convenience is referenced herein by its applicable trademark/service mark SA-ETOIMS, the goals of pain and discomfort relief and improved function are accomplished (as with ATOIMS and ETOIMS) and yet the treatment is totally non-invasive. The use of a needle/pin is avoided and this will greatly improve patient acceptance since the average person has hesitations and/or frank fear of being penetrated multiply with multiple pins or with one pin. SA-ETOIMS has the capacity to help patients in chronic pain on a mass, worldwide scale, as regional and diffuse myofascial pain, e.g., due to aging of the spine causing spondylotic radiculopathy, is a ubiquitous condition.

Procedural difficulties described in needle-applied ETOIMS are avoided with non-invasive SA-ETOIMS. There is no bleeding or tissue trauma in SA-ETOIMS allowing the SA-ETOIMS treatment to be virtually painless (depending on the stimulus strength and duration used) during the treatment. Pre-medications are therefore not needed with SA-ETOIMS and since there is no associated bleeding and bruising to skin and tissues, there is better patient acceptance of the procedure.

In SA-ETOIMS, the treatment time may be drastically reduced. There are no repetitive bimanual stabilizing positions needed of the operator's upper limbs avoiding repetitive stress injuries to the operator. SA-ETOIMS allows treatment to many areas of a patient's body very rapidly in one session. The SA-ETOIMS treatment is very practical in its ability to allow treatment to multiple areas daily and over a chronic period of time to many patients requiring this type of service since the SA-ETOIMS procedure is user friendly to both patient and operator. In contrast, intensive needle-applied ETOIMS is generally provided only 1-2 times/week to allow post treatment pain to subside before the next treatment. Although limited treatments with needle-applied ETOIMS can be done daily, this is done only after careful patient selection and daily treatment is generally not done for the average patient in pain. Therefore, the patients' chronic pain still has to be managed with medications, oftentimes multiple medications have to be used to control the pain. With SA-ETOIMS, since daily treatments are possible, it is envisioned that chronic patients may probably be managed with very low doses of narcotic or non-narcotic medications and/or fewer number of medications. In the case of acute pain, a cure is possible if immediately treated within a day of onset of symptoms. This is due to immediate release of nerve conduction block (neurapraxia) from increased circulation allowed by less tight muscles after SA-ETOIMS treatment. Patients can thus return to full normal activities and the cascade of chronic pain related disabilities are averted.

The training of the ETOIMS technique is now simplified with non-invasive SA-ETOIMS such that it could readily be taught, not only to physicians, but also to paramedical personnel such as chiropractors, physical therapists, nurses and physician assistants.

It is probable that responsible chronic pain patients in long term therapy and their caretakers can be trained and certified to be able to treat at home. Such responsible personnel could treat less involved patients as well as institute treatments earlier, leading to increased prevention of chronic pain. This would result in real savings in direct and indirect health care costs, and the SA-ETOIMS treatment could be offered more effectively to patients and other certified operators on a national and international level. SA-ETOIMS with its non-invasive technology of delivering the electrical stimulus to deep motor end-plate zones is user friendly to both the patient and the operator as previously explained. Thus this technology has an exponential capacity to spread world wide in a shorter period of time. The training time to learn this method is considerably shortened and it is feasible that this method can be trained within 1-2 hours to physicians conversant with anatomy, physiology and peripheral neurology. It is also envisioned that training paramedical personnel in this technique will be easy and can be probably accomplished within 1-2 days. To standardize the outcome of the training received, it will be desirable that all personnel trained be credentialed as operators capable of performing the SA-ETOIMS method.

In contrast to TENS as previously described, in SA-ETOIMS, many motor points may be stimulated one at a time rather than simultaneously, with considerably shorter duration pulse widths of 0.05-0.1 ms. However, in larger muscles that are stiff and tight longer pulse widths 1-2 ms may be needed. The therapeutic twitches with SA-ETOIMS induce an abrupt jumping motion of the muscle area stimulated, in contrast to the TENS pumping motions which are considered not to have much therapeutic value in SA-ETOIMS treatments. An SA-ETOIMS session may generally lasts for 10 to 60 minutes and can be applied daily.

In SA-ETOIMS, it is satisfactory to have only one twitch per stimulated point and the hand-held probe may be moved from one point to the next after a 0.5 second twitch period. A principle of treatment in SA-ETOIMS is to search for the surface motor point that is in continuity with deep motor end-plate zones in the interior of the muscle that produces the therapeutic twitch strong enough to either shake or move the joint upon which the stimulated muscle acts. An SA-ETOIMS session may last for 10 to 60 minutes and can be applied daily.

In SA-ETOIMS, it is satisfactory to have only one twitch per stimulated point and the hand-held probe is moved from one point to the next along intramuscular and intermuscular grooves after a 0.5 second twitch period. SA-ETOIMS uses low frequency (1-2 Hz) and high voltage (400 volts with constant current) applied with a short duration current of 0.1 ms or even as short as 0.05 ms in the case of acute nerve related muscle problems, and may be increased to as long as 1 ms or occasionally for just a few test stimuli up to 2 ms when stimulating the buttock muscles in the case of chronic muscle tightness associated with chronic nerve related muscle disorders. A principle of treatment in SA-ETOIMS is to pass electrical charge through the skin with sufficient intensity in order to be able to search for and identify the surface motor points that are in continuity with motor end-plate zones within the interior of the muscle. Excitation of these motor points produces the therapeutic twitch strong enough to either shake or move the joint upon which the treated muscle acts. This type of twitch is most effective in normalizing nerve and muscle function through exercise and tissue mobilization effects that can lead to increased blood flow to the area stimulated.

Unlike other known electrical muscle stimulators, the present inventor has found that the Digitimer DS7A device (Herforthshire, England) is capable of delivering a suitable surface stimulation of motor points for use in the inventive SA-ETOIMS technique. Since the skin impedance is in the megaohms, to penetrate through the skin resistance in order to produce the stronger and deep twitches needed for therapeutic effects of SA-ETOIMS, a relatively high voltage (e.g., 400 volts) with a constant current (e.g., of 100 milliamp) and short duration current pulses (0.1-0.2 ms on the average) is needed.

SA-ETOIMS preferably provides stimulation at the relatively low rate of for 2 Hz, causing a brief twitch to exercise, stretch and relax the afflicted stimulated point in the muscle. In contrast, electrical muscle stimulators are designed to contract the muscle through causing a muscle spasm by using very high frequency stimulation briefly and then to allow it to relax. If a twitch type contraction is produced at lower frequencies, the twitches are obtained non-specifically and tend to be low amplitude and non-forceful. Thus, this "pumping" motion type twitches will not provide therapeutic effects obtainable with SA-ETOIMS, wherein the stimulated muscle part is caused to actually "jump" in order to shake or move the joint upon which the treated muscle acts.

In SA-ETOIMS, the treatments are preferably performed motor point by motor point along the grooves separating the afflicted muscle from an adjacent muscle or linear grooves within afflicted muscles or along the edges of muscle bands or muscle nodes within afflicted muscles. Electrical muscle stimulators are designed to treat the whole muscle by repetitively contracting and relaxing the muscle continuously for extended periods (20 minutes to one hour) and not by very brief motor point by motor point stimulation as in SA-ETOIMS. In SA-ETOIMS, each motor point may be treated for only 0.5 seconds or briefer to elicit one twitch and if a train of single twitches is needed to fatigue the nerve it may last 2 seconds yielding a total of 4 twitches with 2 Hz stimulation. SA-ETOIMS is not designed to cause muscle spasms. A purpose of SA-ETOIMS is to release muscle spasms by finding the electrically sensitive motor point, causing the muscle fibers at the stimulated area to contract suddenly (twitch) within 0.5 seconds or briefer with the stimulus strength kept constant at all stimulated points within the same muscle after the stimulus strength has been determined following titration to produce the quality of the twitch strength that will at least shake the joint upon which the treated muscle acts. Once this stimulus strength has been determined, it is kept constant to find the motor point where on stimulation the joint will move. This type of twitch causes immediate relaxation through a stretch effect to the stimulated area.

The joint movement in twitches obtainable with SA-ETOIMS is preferably from the contraction of a single muscle. However, stimulus may spread to other motor points of adjacent muscles and the joint movement may be secondary to contraction of several adjacent muscles. Although achieving joint movement is an objective of stimulating the motor point, such movements may not occur when the muscles are very tight or if the muscles treated are not associated with a joint that would be expected to move/jump, as in the case of the paraspinal muscles. In such situations, a motor point to which electrical stimulation may be effectively applied can be identified by twitch forces retrogradely transmitted along the probe which are sufficiently large to be perceptible by feeling the recoil effect that may be strong enough to move the clinician's hand that holds the probe.

The stimulus in SA-ETOIMS is isolated and localized to the motor point and motor end-plates in the region of the electrical stimulus to that single muscle, since the active and reference electrodes of the hand-held probe ideally are both placed on the muscle of interest. The SA-ETOIMS method of motor point stimulation preferably avoids stimulating major peripheral nerves, unlike motor nerve studies where peripheral nerves are sought to be stimulated. Since the objective in SA-ETOIMS is to stimulate motor points, regions where peripheral nerve trunks are located are preferably avoided for stimulation with SA-ETOIMS. The stimulus strength with SA-ETOIMS is preferably stronger than for nerve conduction studies or at least in the range of nerve conduction studies depending on the degree of tightness of the overlying muscles. If a peripheral nerve has been stimulated during the search for the motor point, all muscles supplied by that peripheral nerve will contract, whereas in SA-ETOIMS, generally only the stimulated muscle will contract on stimulating its motor point. SA-ETOIMS may use voltage up to 400 volts with constant current up to 100 milliamps at an average pulse width of 0.1-0.2 ms, and stimulating for 0.5 seconds per stimulus point directly onto the surface of the muscle. The stimulus is applied along the intermuscular and intramuscular grooves and along the edges of the intramuscular muscle bands and muscle nodes or at the tender muscle points. These stimulus capacities used for SA-ETOIMS are not possible with the electromyographic machine used for nerve conduction studies that are limited to constant voltage of 300 volts or constant current of 100 milliamp. The older, outmoded electromyographic (EMG) machines for nerve conduction studies use constant voltage stimulation up to 300 volts for nerve conduction tests. The present inventor had tried this type of EMG machine with maximum voltage up to 300 volts for SA-ETOIMS purposes. However, these machines do not readily evoke a twitch and the stimulus probes produce considerable discomfort at the skin level that is generally unacceptable for motor point stimulation purposes. The newer EMG machines use constant current for nerve stimulation studies. In using this type of EMG machine with maximum stimulus strength of 100 milliamp for SA-ETOIMS purpose, the present inventor finds that a twitch is more readily obtained but there is still considerable skin discomfort which is unacceptable for therapy purposes. The close spacing of bipolar electrodes (usually about 1" apart between active and reference electrodes) is believed to be the chief cause of stimulus pain when using the known EMG machines for SA-ETOIMS; this pain could be alleviated by increasing the spacing.

SA-ETOIMS seeks to provide localized intramuscular electrical stimulation to responsive muscle motor endplate zones, to thereby evoke local, focal and specific muscle twitches caused by contraction of a single stimulated muscle. Very brief focal twitches may be produced in 0.5 s with SA-ETOIMS. With SA-ETOIMS very low frequency stimulation may be used (1-2 Hz). The stimulus is kept constant within the same muscle after the stimulus strength has been determined following titration to produce the quality of the twitch strength that will at least shake the joint upon which the treated muscle acts. Once this stimulus strength has been determined, it is kept constant to find the motor point where on stimulation the joint will move. SA-ETOIMS method preferably avoids stimulation of peripheral nerves and is isolated to stimulation of muscle at motor point by motor point or along linear grooves separating muscles or linear grooves within muscles or along the edges of bands or nodes within muscles. Use of a voltage of 400 volts and constant current of 100 milliamps in SA-ETOIMS provides sufficient stimulus strength to the motor point and motor end-plate zones within the interior of the muscle to evoke the desired twitches. This is not possible or practical with an EMG device for peripheral nerve stimulation that uses a maximum constant voltage of 300 volts or an EMG device that provides constant current of 100 milliamps but is not able to provide a sufficiently high stimulation voltage, e.g., 400 V.

SA-ETOIMS may be performed with the DS 7A model research device from Digitimer Limited (Herforthshire, England); the unit is capable of providing constant current up to 100 mA at a high voltage (up to 400 volts), and a varying pulse widths of 0.05 to 2 ms), for percutaneous stimulation. Since the skin resistance is not an issue due to the brief high voltage stimulation, and the stimulation and reference electrodes can be widely spaced from each other, there is little to no skin discomfort. This combination of stimulus parameters (constant current up to 100 mA and high voltage (up to 400 volts), pulses widths (0.05 ms to 2 ms) for surface stimulation produced the therapeutic twitches for SA-ETOIMS; however, it is probable that a constant voltage stimulator with variable current may also produce the similar twitch elicitation effect.

The surface stimulation method with SA-ETOIMS preferably does not employ any needles, and facilitates the elicitation of twitches at 1-100 treatment points within the afflicted muscle, depending on the size of the muscle. A total of 50 afflicted muscles can be treated with SA-ETOIMS within an average time of 20 minutes. A shorter session of 10 minutes can be used for treating 10 muscles or so on each side of the body. For more difficult cases, treatment times may be longer with a maximum of 60 minutes. Time period of twitching is in the range of 0.5 for 1 twitch and 2 seconds if a train of 4 twitches per stimulated point is to be obtained with 2 Hz stimulation. An embodiment of SA-ETOIMS uses an exposed conductive tip of a surface probe with approximate diameter of 10 mm or less, thus providing localized intramuscular stimulation to the motor points and motor end plate zones. The exposed conductive tip is preferably placed along grooves separating the afflicted muscle from an adjacent muscle or linear grooves within muscles or along the edges of muscle bands or muscle nodes within muscles or at tender points in the muscle. In one embodiment, direct or alternating monophasic electrical current with a fixed amplitude at a frequency of 1 Hz is used for stimulation. The pulse width may be 0.05 ms, 0.1 ms-1.0 ms, or longer. For example, about 5 stimuli may be applied with a 2 ms pulse width in order to test if the motor point can be located easier. Since this is a more painful stimulation, if the motor point cannot be found within five stimuli, the pulse width may be reduced back to 1 ms. The reference electrode may be a surface conductive electrode made of metal or other conductive materials of approximately 25 mm size or can be in the form of straps placed around the distal limbs at forearms, wrists, legs or ankles. Wide-spaced bipolar hand-held probe configurations which are particular well suited for SA-ETOIMS purposes are disclosed in the applicant's provisional application Ser. No. 60/834,184, filed Jul. 31, 2006, entitled: "Bipolar Stimulation/Recording Device With Widely Spaced Electrodes," incorporated by reference herein.

The above and other objects, features and advantages of the present invention will be readily apparent and fully understood from the following detailed description of preferred embodiments, taken in connection with the appended drawing.

BRIEF DESCRIPTION OF THE DRAWING

The single FIGURE is a schematic system view showing electrode placement on/in a patient, and a cross-sectional view of muscle tissue including three adjacent motor end plate zones forming a motor end plate zone region associated with three pre-terminal nerves.

DETAILED DESCRIPTION OF THE PREFERRED EMBODIMENTS

The therapeutic use of electrical stimulation in the management of regional and diffuse myofascial pain due to spondylotic radiculopathies due to aging has previously been described using intramuscular conductive electrodes, namely electrical twitch obtaining intramuscular stimulation (ETOIMS™). See Related Art section, supra. The present physician inventor has found that localized electrical stimulation, to elicit painless twitches, can effectively be used in order to obtain enhanced relief from such pain, through a modified form of ETOIMS, vis, surface-applied electrical twitch obtaining intramuscular stimulation or SA-ETOIMS.

A difference between SA-ETOIMS and needle-applied ETOIMS is in the mode of applying electricity to the motor end-plate zones, the former uses surface application whereas the latter uses needle insertion and withdrawal, or implanted electrodes. Otherwise the indications and contra-indications for use are similar to both. With needle-applied ETOIMS, the treatment is applied at 4-10 points per muscle and 10 muscles on each side of the body are treatable within 10 minutes. It is however, more time efficient, practical, easy and efficacious to treat many more motor points per muscle and more muscles per treatment session with SA-ETOIMS than with needle-applied ETOIMS since SA-ETOIMS is virtually painless since it is non-invasive and passes electricity quickly through the skin to the motor points. Also, many more motor points will readily twitch with SA-ETOIMS since the electrical field on the skin surface will readily reach any responsive motor point within the electrical field.

SA-ETOIMS uses high voltage stimulation, e.g., with pulse widths of 0.05 to 2.0 ms at the motor points, unlike routine surface motor point stimulation that uses minimal-intensity, short duration electrical stimulation. Shorter pulse widths (e.g., 0.05 ms or 0.1-0.2 ms) of low intensity stimulus using very low current strength of <20 mamp at 400 Volts are preferably used with acute nerve related muscle problems. Longer duration pulse widths with high intensity stimulus of 100 mamp at 400 Volts are used in muscle tightness related to chronic nerve related muscle conditions. Any responsive motor points on the skin surface have inherent connections to the motor end-plate zones within the muscle with capacity to cause the deeper parts of the muscle to twitch. The distinct advantage of SA-ETOIMS is its capacity to reach any responsive motor points on the skin surface within its electrical field of the surface probe making it more efficacious in eliciting twitches. It is also capable of getting the deeper layers of the muscle to twitch more readily and has capacity to elicit stronger twitches due to its ability to encompass and excite more motor points per stimulated skin point.

Deep muscle twitches are not possible with electrical acupuncture or PENS or electrically stimulating the acupuncture needle within a metal plunger as in IMS since the acupuncture pins are not strong and firm enough to penetrate deep into the muscle. As such, these three methods of needle stimulation with electricity will produce very small and superficial twitches only. These weak and miniscule twitches are not as therapeutic as the forceful deep twitches elicited with needle-applied ETOIMS. Needle-applied ETOIMS can evoke strong twitches from within the depths of the muscle stimulated since a stronger and stiffer monopolar needle is used for stimulation and this needle is automatically inserted with a device to reach the deeper muscle layers. However when the deep motor endplate zone stimulated is refractory to the electrical stimulus or when the muscle is too tight or too stiff to allow electricity to spread and reach to the responsive motor end plate zones, the needle has to be retracted and re-inserted at another motor point on the skin. This causes unnecessary and undesired pain to the patient, thus making needle-applied ETOIMS less appealing to patients in pain.

A few definitions will facilitate a full understanding of the present inventive method, and its distinction from prior IMS modalities:

Motor end plate: The point, usually at the middle of a single muscle fiber, where the nerve terminal meets the muscle fiber, i.e., the nerve-muscle junction, as seen clearly in muscle fiber A1 in the enclosed FIGURE. The terminal nerves of pre-terminal nerve 1 meets the motor end-plates of all unshaded muscle fibers A, B and C. Similarly, terminal nerves of pre-terminal nerve 2 meets the motor endplates of dark shaded muscle fibers E, F and G and the terminal nerves of pre-terminal nerve 3 meets the motor endplates of hatched muscle fibers H. The region where many motor end-plates are concentrated is termed a motor end-plate zone.

Motor point: Clinically, the point over or slightly within a muscle where a contraction of a muscle may be elicited by a minimal-intensity, short duration electrical stimulation. Anatomically, the motor point corresponds to the locations of the terminal portions of the motor nerve fibers (the motor end-plates). This is the official definition from the American Association of Electrodiagnostic Medicine. Clinically, the motor points are located on the surface or just under the surface of the skin at the point of entry of the nerve into the main muscle. The motor points are depicted in the FIGURE at areas 1, 2 and 3 underlying the contact point Z of the surface probe belonging to pre-terminal nerves 1, 2 and 3.

Twitches: Focal muscle fiber contractions followed immediately by relaxation of the fibers that contracted. They can be obtained by mechanical excitation of the nerve terminal portions (motor end plates), through mechanical agitation or electrical stimulation at the motor end-plate zones.

In the sole FIGURE, the region where the pre-terminal nerves 1, 2 and 3 enter the muscle is the easiest motor point to stimulate because it has the least resistance to electrical stimulation. The pre-terminal nerve is larger than the terminal nerve and is, therefore, easier to stimulate electrically. Clinical motor points are points, like 1 2 and 3, located essentially above or slightly within the muscle where a contraction of muscle fiber may be elicited by a minimal-intensity, short duration electrical stimulation. Clinical motor points do not encompass the deeply situated motor points in the interior of the muscle. These deeper placed motor points or motor end plates within the muscle will not respond to electrical stimulation from points over the muscle using minimal-intensity, short duration electrical stimulation. However, the present inventor has discovered that they will respond to high voltage of 400 volts with constant current of 100 mamps at pulse widths of 0.05-1 ms or occasionally for a few test stimuli up to 2 ms electrical stimulation. For example, about 5 stimuli may be applied with a 2 ms pulse width in order to test if the motor point can be located easier. Since this is a more painful stimulation, if the motor point cannot be found within five stimuli, the pulse width may be reduced back to 1 ms.

Referring to the sole FIGURE, a surface probe is shown making skin contact at Z and also a surface reference electrode is shown. A shallowly inserted acupuncture needle is shown inserted at point X and a larger monopolar needle is shown inserted deeper into muscle at point Y. The motor end plate zones associated with pre-terminal nerve 1 supplies the unshaded muscle fibers A, B and C. The motor end plate zones associated with pre-terminal nerve 2 supplies the dark-shaded muscle fibers E, F and G. The motor end plate zones associated with pre-terminal nerve 3 supplies the hatched muscle fibers.

Point X, where a shallowly inserted acupuncture pin has been placed, is a motor point (clinically speaking), assuming that a contraction can be elicited by a minimal-intensity, short duration electrical stimulation at that point. Since this motor point is close to the surface of the muscle, stimulation directly over the muscle will excite the associated motor end-plates resulting in a twitch from contraction of the muscle fibers. In contrast, point Y in the muscle where the tip of a monopolar EMG pin is placed likely will not elicit a muscle contraction from stimulation over the muscle with minimal-intensity, short duration electrical current because this motor point is deeply situated. Point Y where monopolar pin tip is placed deep in the muscle is an anatomic motor point, i.e., a motor end plate zone. To avoid confusion, the present inventor generally refers to anatomical "motor points" as "motor end plate zones." This convention applies herein. Unless otherwise indicated, references to "motor points" refer to the clinical definition of the same. The present inventive technique of SA-ETOIMS provides electrical stimulation to motor points on the skin surface using high voltage, preferably using a high voltage of 400 volts with constant current of 100 mamps at pulse widths of 0.05-1 ms or, as previously mentioned, in some cases for about 5 stimuli with 2 ms pulse width in order to test if the motor point can be located easier. The electrical stimulation is strong enough to excite the motor point of pre-terminal nerve 1 and its motor end-plate zones. This gives results therapeutically equivalent to, or better than, stimulating at the motor end-plate zones using a deeply placed monopolar needle electrode. In fact, since motor points can be easily excited from the skin surface with SA-ETOIMS, more motor end plate zones can be excited than with needle applied ETOIMS within a given treatment time frame. It is envisioned that better therapeutic effects can be attained with SA-ETOIMS than with needle applied ETOIMS. In contrast, as described in applicant's U.S. Pat. No. 6,058,938, previous attempts to provide intramuscular stimulation (IMS) utilizing a fully exposed pin or surface patch electrified with relatively low voltage were not effective to generate the forceful twitch responses sought-after and obtainable with the applicant's needle applied ETOIMS technique.

Referring to the sole FIGURE, consider the therapeutic effects on stimulating the muscle entry zone of the pre-terminal nerves 1 and 2 (motor point Z) with that obtained by stimulation at motor point X where an acupuncture pin has been placed, and motor end plate zones where the tip of monopolar EMG pin Y has been placed. The best effect is obtained electrically at the point Z where the probe is on the skin surface since the relatively high voltage electrical field can stimulate not only nerves #1 and #2 but also #3. In situations where nerves #1 and #2 may be refractory to the electrical stimulus but nerve #3 is excitable, the electrical field emitted from the surface probe excites nerve #3 with the same stimulus application. Therefore, twitches are more readily evoked with SA-ETOIMS since the electrical field will encompass one or more excitable motor points with each new placement of the surface probe along the linear grooves between and within muscles where motor points lie. However, in this situation where nerves #1 and #2 are refractory to electrical stimulation, at the point Y where the tip of the monopolar pin is placed, the motor end-plate zones at that site belonging to nerves #1 and #2 that innervate the shaded and unshaded muscle fibers, will not produce a twitch. Thus the monopolar pin has to be retracted and re-inserted to be close to the motor end-plate zones of electrically excitable nerve #3 (cross-hatched muscle fibers).

As for the shallowly placed acupuncture pin with its weak electrical field, there will be no twitch elicitation since it is close only to a few motor end plate zones of the shaded muscle fibers belonging to the refractory nerve #2. It is technically difficult to manually re-insert the acupuncture pin since it is too flexible and impractical for such purpose of motor endplate stimulation at multiple sites.

Again referring to the FIGURE, in the situation where nerves #1 and #2 are equally excitable together with nerve #3 to stimulation with the surface probe, all motor end-plate zones of unshaded muscle fibers supplied by nerve #1 and all motor end-plate zones of shaded muscle fibers supplied by nerve #2 as well as all motor end-plate zones of the cross-hatched muscle fibers supplied by nerve #3 will be stimulated resulting in twitching of the muscles fibers supplied by nerves #1 through #3. Hence the twitch will be more forceful than with stimulation with the needle electrode tip placed at position Y whose relatively low voltage whose electrical field may not reach the motor endplate zones of muscle fibers H (hatched in the FIGURE) supplied by nerve #3.

In a preferred SA-ETOIMS method, electrical stimulation of muscle motor points and motor end-plate zones is carried out with an electrical stimulator outputting a fixed amplitude alternating current or direct current with a monophasic square wave, a pulse width of 0.1 ms, and a frequency of 1 Hz. The stimulus parameters are voltage of 400 volts and a constant current of 100 milliamps. Stimulation with constant voltage of more than 400 volts may be used at lower current levels (well below 100 milliamps). Longer pulse widths up to 1-2 ms and a frequency of 2 Hz may also be employed with SA-ETOIMS. The stimulus intensity for motor points preferably remains unchanged for all points within the same muscle while searching for the electrically supersensitive motor point or motor end plate zones that will produce twitch forces strong enough to shake or move the joint over which the treated afflicted muscle acts.

In contrast to needle-applied ETOIMS, the stimulation in SA-ETOIMS is provided locally to one or several closely adjacent target motor end plate zones through a surface probe coated placed at Z and a surface (skin mount) reference electrode. A suitable commercially available research electrical stimulation unit is the DS 7A model device from Digitimer Limited (Herforthshire, England); the unit provides constant current high voltage pulses of brief duration for percutaneous stimulation for purposes of investigation of the electrical activity of nerve and muscle tissue. The output current is continuously variable over the range 0 to 100 mA. Other small portable units can deliver a few milliamps (up to 80 ma) to a very low impedance load (500-1000 ohms)—they can provide stimulation only when used with a needle and not with surface stimulation since the human body impedance is in the megaohms. The Digitimer device provided stimulus parameters with ability to penetrate through the skin resistance to reach the motor points and motor end-plate zones, and can therefore be used to effectively carry-out the inventive SA-ETOIMS technique. It is envisioned that special devices will be made specific and solely for the clinical application of SA-ETOIMS. Such devices are described in applicant's previously referenced provisional application Ser. No. 60/834,184 incorporated by reference herein.

A methodology in accordance with the present invention is now more specifically described. First a motor end plate zone, or region of adjacent motor end plate zones, is located by palpation of an area in the afflicted muscle. Motor end plate zones (and regions of the same) can be identified as rope-like, swollen, lumpy or tender regions along the edges of a myofascial band or nodes within muscle. The motor endplate zones can be stimulated also along the length of intermuscular and intramuscular grooves with the surface probe. These grooves become very visible and easy to follow for further stimulation after the first twitch is elicited with SA-ETOIMS. Due to the localized electrical stimulation, twitch responses are from muscle fibers associated with stimulated motor end plates in one or several adjacent motor end plate zones and are generally obtained immediately upon stimulation with the surface probe.

The twitch responses obtained with SA-ETOIMS tend to be significantly larger and more forceful than those obtained with the previously described methods including needle-applied ETOIMS. Twitches are more readily evoked and larger twitches result from the activation of a greater number of motor end plates, within one or several adjacent zones. This causes the twitching of a correspondingly larger number of associated muscle fibers. It is thus possible to provide a greater amount of pain relief per treatment session. SA-ETOIMS allows many more motor points to be treated per muscle and more muscles to be treated within a treatment time frame comparable to needle-applied ETOIMS. Generally, excellent pain relief effects can be achieved with a stimulus duration of 0.5 s allowing one twitch at 1 Hz at each treatment site. After obtaining a single twitch at a given treatment point within 0.5 s, the conductive surface probe is repositioned manually to another point on the muscle in order to treat another motor end plate zone within the afflicted muscle. Of course, if the muscle is too stiff or too tight due to muscle spasm or has become fibrotic and thus the associated motor end plate zones are refractory to electrical stimulation, twitch responses will not be obtained. If such a condition is determined, either the position of the operator or the patient is changed so that the surface-applied conductive tip can be repositioned to another point on the skin overlying the muscle, preferably along the intermuscular and intramuscular grooves and along the edges of the intramuscular muscle bands and muscle nodes or at the tender muscle points.

Generally, it is recommended that 1-100 treatment sites per muscle be performed depending on the size of the muscle. Treatments are applied at 4-10 or more points per muscle and 10 or more muscles on each side of the body are treatable within 10 minutes.

In searching for the twitch point, a single surface probe is used and if the motor end plate zone is correctly located and is electrically excitable, the treated area should immediately twitch. Otherwise, the point is incorrect, or the muscle is refractory to stimulation, the operator should move and relocate the probe to another point on the skin overlying the muscle or along the intramuscular and intermuscular grooves.

In accordance with the inventive SA-ETOIMS method, the twitching is preferably limited to 0.5 s for one twitch or at most 2 seconds for 4 visible twitches. The twitch responses can be obtained superficial or deep within the muscle depending on the position of the target motor end plate zone or region of adjacent motor end plate zones to be treated. The electrical stimulation is applied locally and focally to one treatment site at a time, with rapid sequential movement between multiple sites to be treated.

With SA-ETOIMS, repetitive bi-manual hand movements of the operator are greatly reduced. Thus, the treatment poses significantly less risk of injury to the operator than does non-electrical manual twitch obtaining IMS. Nonetheless, it is recommended that the treatment be limited to episodes of 10 minutes with an average of twenty minutes. By eliminating or substantially reducing the need for needle penetration or mechanical needle agitation, the patient experiences significantly reduced pain during and after the treatment. Generally, the electrically induced twitches do not cause any discomfort. SA-ETOIMS is relaxing enough that some patients may fall asleep during treatment, something which hardly occurs when performing manual twitch obtaining IMS, or needle-applied ETOIMS due to the pain associated with repeatedly inserting the pin or moving the pin within the muscle. In the latter situations, pre-medications are often used so that the patient can tolerate the treatment procedure. With SA-ETOIMS there is no need for pre-medications.

In addition, with SA-ETOIMS, minimal skill is needed to elicit the twitches because the electrical field can reach and activate multiple motor end-plates with much less precise placement of the treating surface probe in the region of the target motor end plate zone(s). In the inventor's previous needle-applied ETOIMS techniques, more precise placement of the treating pin within or adjacent the target motor end plate zone(s) is necessary to elicit the desired twitch responses.

With SA-ETOIMS, the electricity induces twitches more readily since the electricity can spread to find the path of least resistance, usually very rapidly to stimulate the motor points in the case of recent nerve pathology. Once the electricity is conducted into the muscle tissue, the electricity is easily available to excite electrically susceptible motor end-plate zones that are within the electrical field, even if they are within the depths of the muscle. Therefore, SA-ETOIMS is not only more effective, but less skill is needed on the part of the operator since surface probe placement is not as crucial. The method will be easier to teach and more personnel can be effectively trained.

In addition to their pain relieving effects, the elicited twitch responses can be used diagnostically to determine the state of the innervation of muscles being treated. With fresh nerve irritation, the twitches are forceful; two to three adjacent motor end plate zones may immediately and simultaneously twitch (creating a focal muscle "shudder" or forceful composite twitch) with a single probe application onto the muscle. The twitches may be forceful enough to shake or move the joint where the afflicted muscle being treated is attached.

With chronic nerve irritation, the nerve is not susceptible to stimulation with mechanical stimulation and electrical stimulation is more useful. The inability of the muscle to twitch, even with electrical stimulation, means that the muscle fibers are very tight and taut, may be irreversibly shortened and may have gone into fibrosis. This is especially indicated when with repeated treatments, the muscle is unable to respond by twitching. Reversible muscle shortening due to overwork of the muscle or fresh nerve irritation is muscle spasm. When the muscle is irreversibly shortened, there may be permanent damage of the muscle due to fibrosis.

In its simplest form, the SA-ETOIMS treatment is done manually with a conductive solution or gel applied electrified surface probe (i.e., no guiding structure). With SA-ETOIMS, repetitive stress trauma to the operator from trigger activation of the surface probe with the thumb is a concern, particularly given the large number of treatment points per patient per treatment session. To alleviate such difficulties, it is envisioned that the SA-ETOIMS treatment could be performed using an automatic trigger activator or that the trigger is activated using voice control or other like methods that avoid repetitive manual use of the trigger to initiate electrical stimulation. It is likely that the SA-ETOIMS device will provide a train of pulses cutting down on the number of times needed to activate the trigger. An external trigger that can be initiated by a third person or even by the patient will be useful.

As is generally the case with medical procedures, specialized training and in depth knowledge of the technique on the part of the operator (whether a physician, nurse, physical therapist, chiropractor physician assistant, paramedic or even an experienced patient) is essential in order to achieve beneficial results (and to avoid serious injury to the patient). Along with the above specifications, the following procedural guidelines will enable an operator skilled in IMS therapy to practice the present physician/inventor's SA-ETOIMS modality, focusing on the elicitation of twitch responses by application of localized electrical stimulation to the motor end plate zones.

General Principles

A basic knowledge of anatomy is essential. The trainee is referred to the textbook Gray, H., Anatomy of the Human Body, C M Goss (Ed), Lea & Febiger, Philadelphia, 1995 and to the physician/inventor's textbook: Chu-Andrews J: Electrodiagnosis: An anatomical and clinical approach. J. B. Lippincott, Philadelphia, 1986.

The muscle may be stabilized between the operator's thumb and fingers to facilitate the twitching method.

If twitches are not obtained immediately by at a stimulus point, re-position the muscle or the patient differently and reinstate treatment. The operator also needs to re-position to get the probe in a better direction towards the muscle.

Keep the patient close to the operator. Avoid having to stretch, bending down or leaning over the patient, which may tire and injure the operator's muscles unnecessarily. The elbows of the operator should be kept close to the body and the wrists close to the neutral position.

Treatment sessions should start with 10 minutes or last an average of 20 minutes. Appointments should be spaced with time for rest to avoid repetitive strain injury to the operator.

Patient Contra-Indications—Medical Exclusions from SA-ETOIMS Method of Treatment Patients excluded are those with diseases in which pain is not of neuropathic origin or is too advanced and, therefore, refractory to the SA-ETOIMS method, or those patients for whom such treatment would be contraindicated. These include those patients with:

1. significant disc herniations with spinal nerve root or spinal cord compressions;

2. significant spinal stenosis or spinal instability;

3. pain related to nociception, such as surgically or traumatically induced wounds or fractures;

4. pain related to metabolic or endocrine diseases;

5. pain related to auto-immune diseases;

6. pain related to malignancy;

7. pain secondary to psychiatric causes;

8. skin infections and skin diseases;

9. implants, pacemakers, or pregnancy;

10. inflammatory joint disease;

11. morbid obesity;

12. advanced peripheral neuropathies, or central nervous system diseases; and/or 13. inability to follow instructions or make decisions independently.

Positioning Upper Extremity Muscles for the SA-ETOIMS Treatment

I. Trapezius

A. Supine

In this position, the operator stands at the head of the table.

B. Prone

1. In this position, the operator stands at the head of the table.

2. The patient lies face-down with the arm overhead and slightly abducted.

3. The arm can also be positioned beside the body with hand close to the trunk.

C. Side Position

1. In this position, the operator either stands behind the patient.

2. The patient lies on the side to be treated e.g., the left side is on the lower side for optimal treatment of the left trapezius. The left arm is kept forward at 90.degree to the trunk and the left elbow is bent 90.degree to the arm in the position for external rotation of the left shoulder (Statue of Liberty holding the torch).

3. The opposite right shoulder can be treated from the same position.

a. The right shoulder is placed in internal rotation with the right arm at 90 degree to the trunk and the elbow bent to 90 degree. with the palm of the hand placed flat on the treatment table. The hand is placed at about mid-chest level on the treatment table.

II. Supraspinatus

A. Side Position

1. In this position, the operator is at the head of the table.

2. The patient is positioned lying on the side opposite that to be treated, e.g., side-lying on the left with the right shoulder of the side to be treated uppermost. The right arm is abducted to 90.degree. and elbow bent to 90.degree as in internal rotation to treat the right side. The hand is placed at about mid-chest level with palm down on the examination table.

3. The operator feels for a point one inch medial to the junction of the lateral angle of the spinous process of the scapula and clavicle.

III. Teres Major

A. Side Position

1. In this position, the operator is at the side of the table, standing behind the patient.

2. The patient is positioned as for treating the supraspinatus muscle (see A.2. above).

3. A point which is one inch proximal to the inferior lateral border of the scapula is palpated.

IV. Latissimus Dorsi

A. Side Position

1. In this position, the operator is at the side of the table, standing behind the patient.

2. The patient is positioned lying on the side opposite that which is to be treated. The side to be treated is uppermost.

B. Prone

1. In this position, the operator is at the side of the table on the side to be treated.

C. Supine

1. In this position, the operator is at the side of the table on the side to be treated. The patient's hand may rest on the patient's forehead.

V. Deltoid

A. The operator is positioned at the side of the table on the side to be treated.

B. Supine

1. The patient's arm is positioned 90 degree to the trunk and the elbow is bent 90 degree for the anterior and middle deltoid (Statue of Liberty holding the torch) position.

2. The arm is placed overhead with the elbow bent and the hand on the forehead to treat the posterior deltoid.

C. Prone

1. The operator stands at the head of the table.

2. The patient's arm is positioned overhead and the arm is slightly abducted.

3. The lower part of the posterior deltoid muscle is treated at 1-2 inches lateral to the shoulder joint.

4. The anterior and middle deltoid can be treated at about 2 inches from the shoulder joint.

VI. Triceps

A. The operator is positioned at the side of the patient on the side to be treated.

B. Supine

1. For treating this muscle, the elbow can be extended or flexed. To treat the lower part of the triceps, it is best to have the elbow bent to about 30-40 degree with the hand placed on the lower stomach.

2. The medial and long head head of the triceps can be treated by placing the hand on the forehead with the palm facing up. The operator stands at the angle between the patient's axilla and trunk.

C. Prone

1. The patient's arm is positioned at 90 degree to the trunk and the elbow is bent 90 degree, dropped off over the edge of the table—the fingers are pointing towards the floor.

2. The arm and forearm can be positioned on the bed in the forward stretch position or beside the patient's body with hand close to the trunk.

D. Side Position

1. The patient is positioned on the side opposite that which is to be treated, e.g., the patient lies on the left for treating the right triceps. The right shoulder is abducted to 90 degree and the elbow is bent to 90.degree. The palm of the hand is on the surface of the table.

2. The patient's arm may also be positioned to hang completely off the treatment table.

2. The operator stands in front of the patient.

VII. Infraspinatus

A. The operator is positioned at the side of the table on the side to be treated.

B. Side Position

1. The patient is positioned as described for the teres major and latissimus dorsi muscle treatments. The hand is best placed on the table with the patient slumped forward. The operator stands in front of the patient.

C. Prone

1. The patient lies with the arm abducted to 90 degree and the forearm hanging over the edge of the table.

VIII. Brachioradialis

A. Supine

1. The operator sits beside the patient on the side to be treated.

2. The elbow is flexed to about 30-40 degree with the patient's forearm and hand resting on the lower stomach with palm down. The forearm is between mid-supination and mid-pronation position.

B. Supine

1. The elbow is slightly bent to about 20 degree and the forearm is supinated.

2. The point of stimulation is about 2 cm above the elbow crease along the lateral aspect of the lower arm in the groove made with the junction with the brachialis on the front of the lower arm.

IX. Flexor Carpi Ulnaris and Flexor Digitorum Profundus

A. The operator sits along side of the bed, and the medial border of the patient's forearm is close to the operator.

B. Supine

1. The arm is abducted at the shoulder with the elbow bent and the forearm supinated.

2. The point of stimulation is at the junction of the upper third of the forearm with the lower two-thirds of the forearm.

X. Adductor Pollicis

A. The operator sits along side of the bed on the side to be treated and the patient's hand is close to the operator.

B. Supine

1. The forearm is kept between mid-pronation and mid-supination with the hand resting on its medial border.

2. The muscle is stimulated at the base of the first web space, about the junction of the bases of the first and second metacarpal bones.

C. Supine

1. Alternately, the hand can be placed on the palmar surface, with the forearm pronated.

XI. First Dorsal Interosseous

A. The operator sits along side of the bed on the side to be treated and the patient's hand is close to the operator.

B. Supine

1. The hand is placed on the palmar surface with the forearm pronated.

2. The point of stimulus is about the midpoint of the shaft of the second metacarpal bone.

XII. Abductor Digiti Minimi

A. The operator sits along side of the bed on the side to be treated and the patient's hand is close to the operator.

B. Supine

1. The patient's hand is placed palm down on the table.

XIII. Abductor Pollicis Brevis

A. The operator sits along side of the bed on the side to be treated and the patient's hand is close to the operator.

B. Supine

1. The patient's hand is placed palm up on the table.

XIV. Dorsal Interossei

A. The operator sits along side of the bed on the side to be treated and the patient's hand is close to the operator.

B. Supine

1. The patient's hand is placed palm down on the table.

XV. Sternocleidomastoid

A. Supine

1. The operator stands along side near the head end of the bed on the side to be treated. The patient's head is close to the operator. The patient's face is turned away to the left to treat the right side.

B. Side Position

1. The operator stands along side near the head end of the bed, and the patient's head is close to the operator. The uppermost side is the side to be treated. The face is turned away to the left to treat the right side.

C. Prone

1. The operator stands along side near the head end of the bed on the side to be treated. The patient's head is close to the operator. The patient's face may be kept neutral or is slightly turned away to the left to treat the right side.

XVI. Rhomboid Major

A. Prone

1. In this position, the operator stands at the side of the patient with the patient's side to be treated close to the operator. The patient's arm may be slightly abducted overhead or kept beside the body with the hand beside the buttock.

B. Side Position

1. In this position, the operator stands behind the patient.

2. The patient lies on the side with the side to be treated uppermost. The treatment can be given along the entire medial border of the scapula. The opposite rhomboid major muscle can be treated with the patient in the same position.

3. The patient lies on the side with the side to be treated lowermost. The treatment is directed towards the medial border of the scapula and the entire length of the medial border can be treated. In this position the opposite rhomboid major muscle which will now be uppermost can also be treated.

XVII. Levator Scapulae

A. Prone

1. In this position, the operator stands at the side of the patient with the patient's side to be treated close to the operator. The patient's arm may be slightly abducted overhead or kept beside the body with the hand beside the buttock 2. The patient stretches the shoulder backward and the forearm bent behind the back in a "hammer-lock" position utilized by wrestlers.

B. Side Position

1. In this position, operator stands behind the patient.

2. The patient lies on the side with the side to be treated uppermost. The probe is directed towards the superior angle of the scapula. The opposite levator scapulae muscle can be treated with the patient in the same position.

3. The patient lies on the side with the side to be treated lowermost. The probe is directed towards the superior angle of the scapula. In this position the opposite levator scapulae muscle which will now be uppermost can also be treated.

XVIII. Serratus Anterior

A. Side Position

1. In this position, the operator stands behind the patient.

2. The patient lies on the side with the side to be treated uppermost. The operator places the index finger and middle finger of the non-dominant hand respectively on the intercostal space (space between the ribs) above and below a rib to protect the intercostal space. The dominant hand holds the probe and the probe is directed towards the rib.

Positioning Lower Extremity Muscles for the SA-ETOIMS Treatment

XIX. Gluteus Maximus

A. Prone

1. In this position, the operator stands at the side of the bed close to the side of the patient that is being treated.

2. The myofascial band that transverses along the upper third of the muscle is stimulated. This band is usually located by finding the mid-point between the tip of the coccyx and the posterior superior iliac spine. This mid-point is then joined by a line to the greater trochanter.

3. The point of stimulation is done along this line or just above this line and at the mid-point of the muscle.

4. The probe is held vertical with the direction of the pin towards the surface of the table.

B. Side Position

1. In this position, the operator stands at the side of the bed, in front of the patient, close to patient's limb that is being treated.

2. The patient is positioned on the side opposite that which is to be treated and very close to the edge of the table to be close to the operator, e.g., the patient lies on the left for treatment to the right side. The right hip and knee are bent and crossed forward over the left thigh and leg. The patients' body is also slumped forward. The ischial tuberosity is palpated.

3. Stimulation is performed along the line above the level of the ischial tuberosity.

XX. Gluteus Medius

A. Side Position

1. The operator can stand either in front of or behind the patient.

2. The patient is positioned as for the gluteus maximus muscle (see B.2. above). The patient must be very close to the edge of the table so the operator does not have to strain or lean over to reach the muscle.

3. Stimulation is performed in the outer lateral quadrant of the buttock above the level of the greater trochanter.

XXI. Tensor Fascia Latae

A. Side Position

1. The operator stands in front of the patient.

2. The patient is positioned as for the gluteus maximus muscle (see B.2. above). The treated limb is uppermost and this hip and knee are crossed forward over the other limb. The knee is kept is about 30 degrees of flexion. The patient is close to the edge of the table, close to the operator.

3. The muscle is treated along the edge of the muscle belly starting from the level of the anterior superior iliac spine to the knee and the edge of the muscle will be well-defined as soon as the first twitch is elicited.

B. Supine

1. The operator stands beside the patient close to the patient on the side to be treated.

2. The patient lies with the hip and knee flexed 30 degree. and the knee in the neutral position, pointing towards the ceiling and not rotated.

3. The point of stimulation is about 2 inches distal to the anterior superior iliac spine, in the groove between the tensor fascia latae and the sartorius muscle.

C. Seated

1. The operator may stand at the side of the patient or in front of the patient between the patient's thighs.

2. The patient is seated at the edge of the table with the feet resting on a stool so that the knees are bent slightly higher than the level of the hips. The knees are in the neutral position, pointing towards the ceiling and not rotated outward.

3. The point of stimulation is about 2 inches from the anterior superior iliac spine in the groove mentioned above.

XXII. Rectus Femoris and Sartorius

A. Supine

1. The operator stands close beside the patient.

2. The patient lies with the hip and knee flexed to about 30 degree with the knee in neutral position and not rotated.

B. Side Position

1. The operator stands behind or in front of the patient.

2. The patient lies on the side opposite that which is to be treated. The side to be treated is uppermost e.g., the right is uppermost if this is the side to be treated. The right hip and knee are flexed 45 degree.

XXIII. Vastus Medialis

A. Supine

1. The operator stands beside the patient close to the patient.

2. The hips and knees are slightly bent and hip rotated outward.

B. Side Position

1. The operator stands in front of the patient.

2. The patient lies on the side opposite that which is to be treated. The patient lies on the left side to have the right side treated.

C. Seated

1. The operator may stand at the side of the patient or in front of the patient between the patient's thighs.

2. The patient is seated at the edge of the table with the feet resting on a stool so that the knees are bent slightly higher than the level of the hips. The hip and knee are rotated slightly outward.

XXIV. Vastus Lateralis

A. Supine

1. The operator stands beside the patient.

2. Stimulation point is at the lateral aspect of the thigh.

B. Side Position

1. The operator stands in front or behind the patient.

2. The patient lies on the side opposite that which is to be treated. The patient lies on the left side to have the right side treated.

C. Seated

1. The operator may stand at the side of the patient or in front of the patient between the patient's thighs.

2. The patient is seated at the edge of the table with the feet resting on a stool so that the knees are bent slightly higher than the level of the hips. The hip and knee are rotated slightly outward.

XXV. Semitendinosus

A. Side Position

1. The operator stands in front of the patient.

2. The patient lies on the side opposite that which is to be treated, i.e., the patient lies on the left to have the right side treated.

3. Alternatively, the patient can lie on the side to be treated, e.g., the patient lies on the right to have the right side treated. The right hip and knees are flexed to about 30 degree.

B. Prone.

1. The operator stands at the side of the patient on the side to be treated. Treat from the level of the ischial tuberosity to the knee.

XXVI. Biceps Femoris—Long Head (See above description for Semitendinosus).

XXVII. Biceps Femoris—Short Head

A. Prone

1. The operator stands beside the patient close to the side that is being treated.

2. The treatment point is at medial to the long head of the biceps femoris in the lower one third of the thigh.

XXVIII. Lateral And Medial Gastrocnemius

A. Side Position

1. The operator stands behind the patient.

2. The patient can be positioned on the left side and the legs are slightly spread apart. The left knee is kept bent to 60 degree or so and placed backward in a scissor position with the right leg placed forward with knee slightly bent. This facilitates treatment of the right lateral gastrocnemius muscle and the left medial gastrocnemius muscle, respectively.

3. The right lateral gastrocnemius to be treated is uppermost and is best if the ankle is slightly dorsiflexed (pulled up).

4. The medial gastrocnemius on the left leg is treated in the same fashion.

B. Supine

1. The operator stands at the side of the table, close to the patient.

2. The hips and knees are slightly bent and the ankle pulled upwards in a slightly dorsiflexed position.

XXIX. Adductor Magnus

A. Supine

1. The operator stands beside the patient close to the side that is being treated. The patient's hip and knee are completely flexed so that the knee almost touches the table with the hip in external rotation.

B. Prone

1. The operator must stand close to the patient near the side to be treated.

C. Side Position

1. The operator stands behind the patient.

2. The patient can be positioned on the left side and the legs are spread apart. The left inner thigh is well exposed for treatment of left adductor magnus muscle.

XXX. Tibialis Anterior

A. Supine

1. The operator stands beside the table and close to the patient. The knee and hip is flexed about 45 degree.

XXXI. Abductor Hallucis Muscle

A. Supine

1. The operator stands beside the table and close to the patient. The foot lies on its lateral border.

2. The probe is positioned at the motor point of the muscle which is near the navicular bone.

XXXII. Abductor Digiti Quinti

A. Supine

1. The operator stands beside the table and close to the patient. The foot is in neutral position.

2. The probe is positioned at the motor point of the muscle which is in front of or behind the base of the fifth metatarsal bone.

XXXIII. Interossei

A. Supine

1. The operator stands beside the table and close to the patient. The foot is in neutral position.

2. The hip and knee can be flexed so that the sole of the foot is on the bed or the foot can be in neutral position not supported on the bed. The probe is positioned vertically and between the bases of the metatarsal bones.

XXXIV. Paraspinal Muscles

A. Prone

1. The operator stands beside the patient close to the side that is being treated.

2. The point of stimulation is about 2 cm away from the spinous process.

B. Side-lying position.

To treat the right side, it is best to have the patient lie on the right and to treat the left have the patient lie on the left. The other side which is upper most can also be treated.

C. Seated position: Operator stand behind the patient.

The present invention has been described in terms of preferred and exemplary embodiments thereof. Numerous other embodiments, modifications and variations within the scope and spirit of the appended claims will occur to persons of ordinary skill in the art from a review of this disclosure.

The invention claimed is:

1. A method of administering non-invasive intramuscular stimulation therapy through use of surface applied electrical stimulation, comprising:
    (A) locating a surface motor point or motor end plate zone or region of adjacent motor end plate zones within the interior of an afflicted muscle of a patient;
    (B) placing a conductive member of an electrical stimulator on the surface of the skin at a position overlying the surface motor point or motor end plate zone or region of adjacent motor end plate zones within the interior of the muscle;
    (C) providing localized electrical stimulation to the surface motor point and an associate motor end plate zone or region of motor end plate zones within the interior of the afflicted muscle, by conducting an electrical current through said conductive member, and flowing from said member through the skin, into said motor end plate zone or region of motor end plate zones within the interior of the muscle, and to a reference electrode on the skin spaced from said conductive member, said electrical stimulation being of sufficient intensity to elicit a forceful twitch response from the muscle fibers associated with motor end plates within said motor end plate zones within the interior of the muscle, unless said motor end plate zones are refractory to electrical stimulation; and
    (D) repeating steps (A)-(C) to elicit a forceful twitch response from muscle fibers associated with additional motor end plates within the interior of the muscle corresponding to an additional treatment point on the afflicted muscle.

2. A method according to claim 1, wherein steps A-C are repeated to elicit twitches from at least four treatment points within the afflicted muscle.

3. A method according to claim 1, wherein said twitch response shakes or moves a joint upon which the afflicted muscle acts.

4. A method according to claim 1, wherein said conductive member of the electrical stimulator is held generally stationary while said localized electrical stimulation is provided in step (C).

5. A method according to claim 1, wherein steps (A) through (C) are repeated to elicit twitches at 4-100 individual treatments point within the afflicted muscle.

6. A method according to claim 1, wherein steps (A) through (D) are repeated to treat a plurality of afflicted muscles within a treatment session.

7. A method according to claim 1, wherein step (C) electrical stimulation is provided to elicit twitching for a time period of between approximately 0.5 s and 2.0 s.

8. A method according to claim 7, wherein between 1 and 4 forceful twitches are elicited in said time period of twitching.

9. A method according to claim 1, wherein the surface stimulation of muscle is performed with a voltage intensity of 400 volts.

10. A method according to claim 9, wherein the surface stimulation of muscle is performed with a constant current stimulation of 100 milliamperes or less.

11. A method according to claim 1, wherein the surface stimulation of muscle is performed using a stimulus pulse width of between 0.1 ms and 0.2 ms.

12. A method according to claim 1, wherein said electrical current is direct current.

13. A method according to claim 1, wherein said electrical current is alternating current.

14. A method according to claim 1, wherein said current is fixed amplitude current.

15. A method according to claim 1, wherein the current is in the form of a monophasic square wave.

16. A method according to claim 1, wherein said current is applied to the motor point or motor end-plate zones in pulses at a frequency of 1-2 Hz.

17. A method according to claim 1, wherein in step (A), the locating of a motor point or motor end plate zone or region of adjacent motor end plate zones within the afflicted muscle of a patient is performed by identifying on a limb or trunk surface linear grooves separating muscles, linear grooves within muscles or edges of bands or nodes within a muscle, and in step (B) the conductive member tip is placed along the identified linear grooves separating muscles, linear grooves within muscles or the edges of the bands or nodes within a muscle grooves separating the afflicted muscle from an adjacent muscle.

18. A method of administering non-invasive intramuscular stimulation through use of surface applied electrical stimulation, comprising applying from a skin surface electrical stimulation of unchanged intensity at multiple points overlying the same muscle in order to locate electrically sensitive motor points or motor end plate zones that will produce twitch forces strong enough to shake or move the joint upon which the treated afflicted muscle acts, said stimulation being provided at each of said multiple points for a period of up to 0.5 seconds for producing one twitch, or for a period of up to two seconds for producing four twitches.

19. A method according to claim 18, wherein said method is applied as an intramuscular stimulation therapy to relieve nerve related muscle pain.

20. A method according to claim 18, wherein said method is applied as a diagnostic aid for differentiating acute or chronic nerve related muscle disorders.

* * * * *